United States Patent
Parikh et al.

(10) Patent No.: US 11,878,081 B1
(45) Date of Patent: Jan. 23, 2024

(54) PHARMACEUTICAL FORMULATIONS OF TAFAMIDIS

(71) Applicant: TaP Pharmaceuticals, AG, Baar (CH)

(72) Inventors: Nilesh Parikh, Irvine, CA (US); William Hite, Winchester, CA (US)

(73) Assignee: TaP Pharmaceuticals AG, Baar (CH)

( * ) Notice: Subject to any disclaimer, the term of this patent is extended or adjusted under 35 U.S.C. 154(b) by 0 days.

(21) Appl. No.: 18/088,382

(22) Filed: Dec. 23, 2022

(51) Int. Cl.
*A61K 9/48* (2006.01)
*A61K 31/423* (2006.01)

(52) U.S. Cl.
CPC .......... *A61K 9/4866* (2013.01); *A61K 9/4858* (2013.01); *A61K 31/423* (2013.01)

(58) Field of Classification Search
CPC ... A61K 31/423; A61P 25/00; C07B 2200/13; C07D 263/05
See application file for complete search history.

(56) References Cited

U.S. PATENT DOCUMENTS

| | | |
|---|---|---|
| 9,770,441 B1 | 9/2017 | Girard et al. |
| 11,208,391 B2 | 12/2021 | Barseghyan et al. |
| 11,523,993 B1 * | 12/2022 | Shanmugam ........ A61K 9/2013 |
| 2021/0363116 A1 | 11/2021 | Chen et al. |
| 2022/0259162 A1 | 8/2022 | Matecic Musanic et al. |

FOREIGN PATENT DOCUMENTS

| | | |
|---|---|---|
| WO | 2009027452 A2 | 3/2009 |
| WO | 2013168014 A1 | 11/2013 |
| WO | 2021001858 A1 | 1/2021 |
| WO | 2021019448 A1 | 4/2021 |
| WO | 2022084790 A1 | 4/2022 |
| WO | 2021152623 A1 | 8/2022 |

OTHER PUBLICATIONS

Pfizer Labs, "Highlights of Prescribing Information VYNDAMAX and VYNDAQEL", Issued May 2019, 16 pages.

* cited by examiner

*Primary Examiner* — Savitha M Rao

(57) ABSTRACT

Certain embodiments of the present disclosure provide pharmaceutical, unit-dose formulations, suitable for oral administration, that contain from 1% w/w to 20% w/w of a tafamidis-organic acid (such as adipic acid, glutaric acid, or fumaric acid) co-crystal; from 0.25% w/w to 2.5% w/w of an organic acid dissolution enhancer. Such formulations release, within 15 minutes in ¾ strength FeSSIF pH 5.8 or in FaSSIF+0.1% polysorbate 80 pH 6.5, at least 85% of the total tafamidis of the formulation.

12 Claims, No Drawings

PHARMACEUTICAL FORMULATIONS OF TAFAMIDIS

FIELD

The instant disclosure provides pharmaceutical formulations, suitable for oral administration, that comprise a tafamidis-organic acid co-crystal, which comprises tafamidis and an additional acid (such as, without limitation, fumaric acid), and methods of making and using same. Such formulations exhibit at least one property of an increased rate and/or extent of dissolution into liquid media such as, without limitation, fed state simulated intestinal fluid ("FeSSIF") and fasted state simulated intestinal fluid ("FaSSIF").

BACKGROUND

Tafamidis is a selective stabilizer of transthyretin. It has an empirical formula of $C_{14}H_7Cl_2NO_3$, a molecular weight of 308.12 g/mol, and a structural formula of:

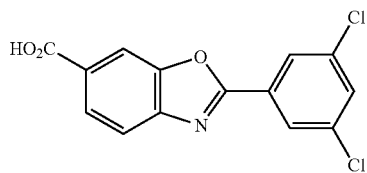 [SMILES: O=C(O)c1ccc2nc(-c3cc(Cl)cc(Cl)c3)oc2c1]

Tafamidis is alternatively known by its IUPAC name 2-(3,5-dichlorophenyl)-1,3-benzoxazole-6-carboxylic acid, and by its CAS Registry Number 594839-88-0. It is the main active pharmaceutical ingredient in a commercial formulation of crystalline 2-(3,5-dichlorophenyl)-1,3-benzoxazole-6-carboxylic acid encapsulated in a soft gel capsule provided under the trade name VYNDAMAX® and indicated for the treatment of the cardiomyopathy of wild-type or hereditary transthyretin-mediated amyloidosis in adults to reduce cardiovascular mortality and cardiovascular-related hospitalization.

United States Patent Application Publication No. 2021/0363116 (the "'116 publication") discloses crystalline forms of tafamidis. The '116 publication states that U.S. Pat. No. 9,770,441 (the "'441 patent") teaches tafamidis forms 1, 2, 4, and 6, of which form 2 is a tetrahydrofuran solvate and forms 4 and 6 are unstable, such that forms 2, 4, and 6 are unsuitable for drug development. The '116 publication asserts that tafamidis form 1 of the '441 patent is more stable than forms 2, 4, and 6, but has low solubility. The '116 publication further states that U.S. Pat. No. 11,208,391 discloses a crystalline, acetic acid solvate form of tafamidis, which was found unstable in drug product. The '116 publication states that, to overcome disadvantages of the prior art it provides fumaric acid, glutaric acid, and adipic acid co-crystals of tafamidis. In particular, those tafamidis co-crystals have good stability, high solubility, low hygroscopicity, high dissolution, which solve the problems in the prior arts and are of great significance for the development of drugs containing tafamidis.

In its Example 6, the '116 publication discloses side-by-side comparative experiments of the solubility of its tafamidis-fumaric acid co-crystal with the 441 patent-taught tafamidis crystal form 1 in simulated gastric fluid ("SGF"), fed-state simulated intestinal fluid ("FeSSIF"), and fasted-state simulated intestinal fluid ("FaSSIF"). The '116 publication states that solubility in these media is close to in vivo solubility. It specifies that 20 mg of its tafamidis-fumaric acid co-crystal and 20 mg of 441 patent-taught tafamidis crystal form 1 were suspended into 3.0 mL of SGF, 3.0 mL of FaSSIF, and 3.0 mL of FaSSIF to get saturated solutions. After equilibration for 1 h, concentrations (μg/mL) of tafamidis in the saturated solutions were measured by ultra-high performance liquid chromatography. The results are listed in Table A, which reproduces the 116 publication's Table 7:

TABLE A

| Medium | '116 publication's tafamidis-fumaric acid co-crystal | '441 patent's tafamidis crystal form 1 |
|---|---|---|
| SGF | 5.6 ug/mL | 1.5 ug/mL |
| FeSSIF | 6.0 ug/mL | 0.6 ug/mL |
| FaSSIF | 11.5 ug/mL | 9.0 ug/mL |

In its Example 12, the '116 publication discloses side-by-side comparative experiments for the dissolution profiles of tafamidis formulations filled into 0 #gelatin capsules. The formulations are disclosed in Tables B and C, which reproduce the 116 publication's Tables 13 and 14:

TABLE B

| Component | mg/unit | % w/w | Function |
|---|---|---|---|
| Tafamidis-fumaric acid co-crystal | 72.5 | 12.08 | API |
| PEG 400 | 390.8 | 65.13 | Diluent |
| Fumaric acid | 16.1 | 2.68 | Stabilizer |
| Povidone K30 | 20.0 | 3.33 | Suspending agent |
| Dibutylhydroxytoluene | 0.6 | 0.1 | Antioxidant |
| Polysorbate 80 | 100 | 16.67 | Surfactant |
| Total | 600 | 100 | |

Note:
72.5 mg of tafamidis-fumaric acid co-crystal is equivalent to 61 mg of tafamidis.

TABLE C

| Component | mg/unit | % w/w | Function |
|---|---|---|---|
| 441 patent's tafamidis crystal form 1 | 61 | 10.17 | API |
| PEG 400 | 402.3 | 67.05 | Diluent |
| Fumaric acid | 16.1 | 2.68 | Stabilizer |
| Povidone K30 | 20.0 | 3.33 | Suspending agent |
| Dibutylhydroxytoluene | 0.6 | 0.1 | Antioxidant |
| Polysorbate 80 | 100 | 16.67 | Surfactant |
| Total | 600 | 100 | |

Tables D and E below are the '116 publication's disclosure, in its Tables 15 and 16, of dissolution experimental conditions and results for the tafamidis formulations set forth in above Tables B and C.

TABLE D

| | |
|---|---|
| Equipment | Sotax AT7 |
| Method | Paddle |
| Dose | 61 mg |
| Volume | 900 ml |
| Speed | 50 RPM |
| Temperature | 37° C. |
| Sampling point | pH 6.8 PBS: 0, 5, 10, 15, 20, 30, 45, 60 min |
| Media replenishment | No |

TABLE E

| Time (min) | '441 patent's tafamidis crystal form 1 | '116 publication's tafamidis-fumaric acid co-crystal |
| --- | --- | --- |
| | Cumulative drug release (%) | |
| 0 | 0.0 | 0.0 |
| 5 | 14.0 | 6.6 |
| 10 | 27.3 | 67.6 |
| 15 | 29.1 | 82.8 |
| 20 | 28.1 | 88.4 |
| 30 | 27.6 | 89.1 |
| 45 | 26.8 | 87.4 |
| 60 | 21.8 | 86.4 |

SUMMARY

Embodiments of the present disclosure provide pharmaceutical, unit-dose formulations, suitable for oral administration that contain from 1% w/w to 20% w/w of a tafamidis-fumaric acid co-crystal; and from 0.25% w/w to 2.5% w/w of an added organic acid dissolution enhancer. Such formulations formulation release, within 15 minutes in modified FeSSIF pH 5.8 or in modified FaSSIF pH 6.5, at least 85% of the total tafamidis of the formulation. Some such formulations further contain one or more of (i) from 77.5% w/w to 82.5% w/w of a polyethylene glycol (PEG), wherein the PEG has a molecular weight of 100 to 1000, (ii) from 0.25% w/w to 2.75% w/w of a polyvinylpyrrolidone (PVP), wherein the PVP has a K value of 10 to 120, (iii) from 1% w/w to 10% w/w of a polysorbate that is polysorbate 20, polysorbate 40, polysorbate 60, polysorbate 80, or a combination thereof, and (iv) from 0.05% w/w to 0.25% w/w of a preservative, for example dibutylhydroxytoluene. In some of such formulations, the organic acid dissolution enhancer is acetic acid, adipic acid, ascorbic acid, benzoic acid, butanoic acid, citric acid, formic acid, fumaric acid, maleic acid, glutaric acid, hexanedioic acid, lactic acid, malonic acid, trichloroacetic acid, oxalic acid, propionic acid, sorbic acid, tartaric acid, and succinic acid, or a combination of at least two of any thereof. In some of such formulations, the formulation comprises two or more of (i), (ii), (iii) and (iv). In some such formulations, the formulation comprises three or all of (i), (ii), (iii) and (iv). In some of such formulations, the PEG has a molecular weight of 400, the PVP is PVP K90, and the polysorbate is the polysorbate 20. Some of such formulations release, within 15 minutes in modified FeSSIF pH 5.8 or in modified FaSSIF pH 6.5, at least 90% of the total tafamidis of the formulation.

Embodiments of the present disclosure provide methods of treating cardiomyopathy or peripheral neuropathy arising from transthyretin amyloidosis, comprising orally administering a unit-dose formulation the disclosure to a subject presenting cardiomyopathy or peripheral neuropathy arising from transthyretin amyloidosis. In some embodiments, the formulations are administered to the subject once daily and the unit-dose formulation comprises from 10 mg to 80 mg tafamidis.

Embodiments of the present disclosure provide pharmaceutical, unit-dose formulations, suitable for oral administration, that contain: from 1% w/w to 20% w/w of a tafamidis-fumaric acid co-crystal; from 77.5% w/w to 82.5% w/w of a PEG that has a molecular weight of 100 to 1000; from 0.25% w/w to 2.5% w/w of an added organic acid dissolution enhancer that is fumaric acid; from 0.25% w/w to 2.75% w/w of a PVP, wherein the PVP has a K value of 10 to 120; from 1% w/w to 10% w/w of a polysorbate that is polysorbate 20, polysorbate 40, polysorbate 60, polysorbate 80, or a combination thereof, and from 0.05% w/w to 0.25% w/w of a dibutylhydroxytoluene. Such formulations release, within 15 minutes in modified FeSSIF pH 5.8 or in modified FaSSIF pH 6.5, at least 85% of the total tafamidis of the formulation. Some of such formulations further contain from 0.05% w/w to 0.25% w/w of a dibutylhydroxytoluene. In some of such formulations, the PEG has the molecular weight of 400, the PVP has the K value of 90, and the polysorbate is the polysorbate 20.

Embodiments of the present disclosure provide pharmaceutical, unit-dose formulations, suitable for oral administration, that contain: from 7.5% w/w to 12.5% w/w of a tafamidis-fumaric acid co-crystal; from 77.5% w/w to 82.5% w/w of a PEG 400; from 0.25% w/w to 2.5% w/w of a fumaric acid; from 0.25% w/w to 2.75% w/w of a PVP K 90; from 1% w/w to 10% w/w of a polysorbate 20; and from 0.05% w/w to 0.25% w/w of a dibutylhydroxytoluene. Such formulations release, within 15 minutes in modified FeSSIF pH 5.8 or in modified FaSSIF pH 6.5, at least 85% of the total tafamidis of the formulation.

Formulations of the present disclosure include Embodiment A.1 to A.7. Embodiment A.1: A pharmaceutical, unit-dose formulation, suitable for oral administration, comprising: from 1% w/w to 20% w/w of a tafamidis-fumaric acid co-crystal; and at least two of (i) from 0.25% w/w to 2.5% w/w of an added organic acid dissolution enhancer; (ii) from 77.5% w/w to 82.5% w/w of a PEG, wherein the PEG has a molecular weight of 100 to 1000; (iii) from 0.25% w/w to 2.75% w/w of a polyvinylpyrrolidone (PVP), wherein the PVP has a K value of 10 to 120; and (iv): from 1% w/w to 10% w/w of a polysorbate that is polysorbate 20, polysorbate 40, polysorbate 60, polysorbate 80, or a combination thereof, wherein the formulation releases, within 15 minutes in modified FeSSIF pH 5.8 or in modified FaSSIF pH 6.5, at least 85% of the total tafamidis of the formulation. Embodiment A.2: The formulation Embodiment A.1, wherein the formulation comprises at least three of (i), (ii), (iii), and (iv). Embodiment A.3: The formulation of Embodiments A.1 or A.2, wherein the formulation comprises all of (i), (ii), (iii), and (iv). Embodiment A.4: The formulation of Embodiments A.1, A.2, or A.3 wherein the organic acid dissolution enhancer is fumaric acid, the PEG has the molecular weight of 400, the PVP is K90, and the polysorbate is the polysorbate 20. Embodiment A.5: The formulation of Embodiment A.1, A.2, A.3 or A.4 that further comprises from 0.001% w/w to 5.0% of a preservative. Embodiment A.6, The Embodiment A.5, wherein the preservative is dibutylhydroxytoluene.

Embodiment A.6: The formulation of Embodiment A.1, A.2, A.3, A.4, A.5 or A.6, wherein the formulation releases, within 15 minutes in modified FeSSIF pH 5.8 or in modified FaSSIF pH 6.5, at least 90% of the total tafamidis of the formulation.

Embodiments A.7 and A.8 relate to methods for use of the formulations of Embodiments A.1 to A.6 to treat a subject. Embodiment A.7: A method of treating cardiomyopathy or peripheral neuropathy arising from transthyretin amyloidosis, comprising orally administering the unit-dose formulation of one of Embodiments A.1, A.2, A.3, A.4, A.5 or A.6 to a subject presenting cardiomyopathy or peripheral neuropathy arising from transthyretin amyloidosis. Embodiment A.8: The method of Embodiment A.7, wherein the formulation is administered to the subject once daily and wherein the unit-dose formulation comprises from 10 mg to 80 mg tafamidis.

Formulations of the present disclosure include Embodiments B.1 to B.5. Embodiment B.1: A pharmaceutical, unit-dose formulation, suitable for oral administration, comprising: from 1% w/w to 20% w/w of a tafamidis-glutaric acid co-crystal; and at least two of (i) from 0.25% w/w to 2.5% w/w of an added organic acid dissolution enhancer; (ii) from 77.5% w/w to 82.5% w/w of a PEG, wherein the PEG has a molecular weight of 100 to 1000; (iii) from 0.25% w/w to 2.75% w/w of a polyvinylpyrrolidone (PVP), wherein the PVP has a K value of 10 to 120; and (iv): from 1% w/w to 10% w/w of a polysorbate that is polysorbate 20, polysorbate 40, polysorbate 60, polysorbate 80, or a combination thereof, wherein the formulation releases, within 15 minutes in modified FeSSIF pH 5.8 or in modified FaSSIF pH 6.5, at least 85% of the total tafamidis of the formulation. Embodiment B.2: The formulation Embodiment B.1, wherein the formulation comprises at least three of (i), (ii), (iii), and (iv). Embodiment B.3: The formulation of Embodiment B.1 or B.2, wherein the formulation comprises all of (i), (ii), (iii), and (iv). Embodiment B.4: The formulation of Embodiment B.1, B.2, or B.3 wherein the organic acid dissolution enhancer is glutaric acid, the PEG has the molecular weight of 400, the PVP is K90, and the polysorbate is the polysorbate 20. Embodiment B.5: The formulation of Embodiment B.1, B.2, B.3, or B.4, wherein the formulation releases, within 15 minutes in modified FeSSIF pH 5.8 or in modified FaSSIF pH 6.5, at least 90% of the total tafamidis of the formulation.

Uses of the formulations of Embodiments B.1 to B.5 to treat a subject are described by Embodiments B.6 and B.7. Embodiment B.6: A method of treating cardiomyopathy or peripheral neuropathy arising from transthyretin amyloidosis, comprising orally administering the unit-dose formulation of one of Embodiments B.1, B.2, B.3, B.4, or B.5 to a subject presenting cardiomyopathy or peripheral neuropathy arising from transthyretin amyloidosis. Embodiment B.7: The method of Embodiment B.6, wherein the formulation is administered to the subject once daily and wherein the unit-dose formulation comprises from 10 mg to 80 mg tafamidis.

Formulations of the present disclosure include Embodiments C.1 to C.6. Embodiment C.1: A pharmaceutical, unit-dose formulation, suitable for oral administration, comprising: from 1% w/w to 20% w/w of a tafamidis-adipic acid co-crystal; and at least two of (i) from 0.25% w/w to 2.5% w/w of an added organic acid dissolution enhancer; (ii) from 77.5% w/w to 82.5% w/w of a PEG, wherein the PEG has a molecular weight of 100 to 1000; (iii) from 0.25% w/w to 2.75% w/w of a polyvinylpyrrolidone (PVP), wherein the PVP has a K value of 10 to 120; and (iv): from 1% w/w to 10% w/w of a polysorbate that is polysorbate 20, polysorbate 40, polysorbate 60, polysorbate 80, or a combination thereof, wherein the formulation releases, within 15 minutes in modified FeSSIF pH 5.8 or in modified FaSSIF pH 6.5, at least 85% of the total tafamidis of the formulation. Embodiment C.2: The formulation Embodiment C.1, wherein the formulation comprises at least three of (i), (ii), (iii), and (iv). Embodiment C.3: The formulation of Embodiment C.1 or C.2, wherein the formulation comprises all of (i), (ii), (iii), and (iv). Embodiment C.4: The formulation of Embodiment C.1, C.2, or C.3 wherein the organic acid dissolution enhancer is adipic acid, the PEG has the molecular weight of 400, the PVP is K90, and the polysorbate is the polysorbate 20. Embodiment C.5: The formulation of Embodiment C.1, C.2, C.3, or C.4, wherein the formulation releases, within 15 minutes in modified FeSSIF pH 5.8 or in modified FaSSIF pH 6.5, at least 90% of the total tafamidis of the formulation.

Use of the formulation of Embodiments C.1 to C.5 in a method of treatment of a subject are described in Embodiment C.6 and C.7. Embodiment C.6: A method of treating cardiomyopathy or peripheral neuropathy arising from transthyretin amyloidosis, comprising orally administering the unit-dose formulation of one of Embodiments C.1, C.2, C.3, C.4, or C.5 to a subject presenting cardiomyopathy or peripheral neuropathy arising from transthyretin amyloidosis. Embodiment C.7: The method of Embodiment C.6, wherein the formulation is administered to the subject once daily and wherein the unit-dose formulation comprises from 10 mg to 80 mg tafamidis.

Embodiments D.1 to D.3 of the present disclosure provide the use of tafamidis to prepare a unit-dose medicament for treatment of peripheral neuropathy or cardiomyopathy of wild-type or hereditary transthyretin-mediated amyloidosis. Embodiment D.1: A method of making a unit-dose formulation of tafamidis, comprising: (i) adding to a vessel having a magnetic stir bar from 77.5% w/w to 82.5% w/w of a polyethylene glycol (PEG), wherein the PEG has a molecular weight of 100 to 1000; (ii) adding to the PEG from 1% w/w to 10% w/w of a polysorbate that is polysorbate 20, polysorbate 40, polysorbate 60, polysorbate 80, or a combination thereof, and continuing mixing until a first clear solution is obtained; (ii) adding from 0.25% w/w to 2.75% w/w of a polyvinylpyrrolidone (PVP), wherein the PVP has a K value of 10 to 120, under continuous mixing and continuing mixing until a second clear solution is obtained; (iii) adding to the second clear solution from 1% w/w to 20% w/w of a tafamidis-fumaric acid co-crystal and from 0.25% w/w to 2.5% w/w of an organic acid dissolution enhancer, under continuous mixing and continuing mixing until a capsuling mixture having a uniform distribution of the tafamidis co-crystal is obtained; and (iv) encapsulating the capsuling mixture.

Embodiment D.2: The method of Embodiment D.1, wherein the organic acid dissolution enhancer is acetic acid, adipic acid, benzoic acid, butanoic acid, fumaric acid, formic acid, maleic acid, glutaric acid, hexanedioic acid, hydrofluoric acid, hydrogen sulfide, trichloroacetic acid, oxalic acid, phosphoric acid, polyester, pentenedeioic acid, sulfurous acid, or a combination of at least any two thereof.

Embodiment D.3: The method of Embodiment D.1 or D.2, further comprising between steps (iii) and (iv) a step (iiia) of adding from 0.001% w/w to 5.0% of a preservative under continuous mixing and continuing mixing until a second clear solution is obtained.

Embodiment D.4: The method of Embodiment D.3, wherein the preservative is dibutylhydroxytoluene.

The total amount of tafamidis in some unit dose formulations of the present disclosure, including without limitation as described in Embodiments A, B, and C is 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, or ranges therebetween.

These and other embodiments are described in further detail below. The detailed description and examples provided herewith depict various embodiments of this disclosure for purposes of illustration only. One skilled in the art will readily recognize from the following discussion that alternative embodiments of the structures and methods illustrated herein may be employed without departing from the principles of embodiments described herein.

DETAILED DESCRIPTION

The present disclosure provides pharmaceutical formulations, suitable for oral administration, comprising a tafamidis co-crystal and an organic acid (e.g., fumaric acid, glutaric acid, or adipic acid). Such formulations of the disclosure are useful for treating cardiomyopathy of wild-type or hereditary transthyretin-mediated amyloidosis to reduce cardiovascular mortality and cardiovascular-related hospitalization.

The present disclosure is based on the inventors' discovery that pharmaceutical formulations consistent with those disclosed herein unexpectedly exhibit an increased rate and/or extent of dissolution in fed state simulated intestinal fluid ("FeSSIF"), fasted state simulated intestinal fluid ("FaSSIF"), or the like. In some embodiments, a formulation of the disclosure can release, in fifteen minutes or less, at least 85%, preferably at least 87.5%, and more preferably at least 90% of the tafamidis of the formulation in the dissolution assay described in Example 1. In some embodiments, a formulation of the disclosure releases, in fifteen minutes or less, from 85% to 95%, from 85% to 92.5%, from 90% to 95%, or from 90% to 92.5% of the tafamidis of the formulation, in the dissolution assay described in Example 1. In some embodiments, a formulation of the disclosure can release, in twenty minutes or less, at least 87.5%, preferably at least 90%, and more preferably at least 92.5% of the tafamidis of the formulation, in the dissolution assay described in Example 1. In some embodiments, a formulation of the disclosure releases, in forty-five minutes or less, at least 90%, preferably at least 92.5%, and most preferably at least 95% of the tafamidis of the formulation, in the dissolution assay described in Example 1. In some embodiments, a formulation of the disclosure releases, in twenty minutes or less, from 85% to 97.5%, from 90% to 97.5%, from 92.5% to 97.5%, from 85% to 95%, from 90% to 95%, or from 92.5% to 95% of the tafamidis of the formulation, in the dissolution assay described in Example 1.

Formulations as disclosed herein can "comprise" a list of ingredients, such list then being open to inclusion of further unspecified ingredients. Alternatively, formulations as disclosed herein can "consist of" a list of ingredients, meaning that the formulations include only the listed ingredients. Formulations as disclosed herein can also "consist essentially of" the listed ingredients, meaning that the formulations include all of the listed ingredients, and may include as well any further ingredients that do not affect the utility of the formulation.

In some embodiments, formulations of the present disclosure can include a tafamidis-organic acid co-crystal, or a pharmaceutically acceptable salt thereof, in weight to weight proportions of the overall formulation of from 1% w/w to 30% w/w and exemplary particular weight to weight proportions include 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 25% w/w, 26% w/w, 27% w/w, 28% w/w, 29% w/w, and 30% w/w, as well as in a range between any two of said tafamidis-organic acid co-crystal proportions.

In some embodiments, tafamidis-organic acid co-crystal added to a formulation of the present disclosure possesses an initial purity of the tafamidis-organic acid co-crystal of at least 90% w/w, for example at least: 90% w/w, 91% w/w, 92%, 93% w/w, 94% w/w, 95% w/w, 96% w/w, 97% w/w, 98% w/w, or 99% w/w.

In some embodiments, formulations of the disclosure can include an organic acid dissolution enhancer. Organic acid dissolution enhancers useful in certain formulations of the disclosure include acetic acid, adipic acid, ascorbic acid, benzoic acid, butanoic acid, citric acid, formic acid, fumaric acid, maleic acid, glutaric acid, hexanedioic acid, lactic acid, malonic acid, trichloroacetic acid, oxalic acid, propionic acid, sorbic acid, tartaric acid, and succinic acid. Formulations of the disclosure may comprise organic acid dissolution enhancer in weight to weight proportions of the overall formulation of 0.05% w/w, 0.1% w/w, 0.5% w/w, 0.75% w/w, 1% w/w, 1.5% w/w, 2% w/w, 2.5% w/w, 3% w/w, 4% w/w, 5% w/w, 7.5% w/w, 10% w/w, 12.5% w/w, 15% w/w, 17.5% w/w, 20% w/w, 22.5% w/w, 25% w/w of the formulation, or in a range between any two of the stated organic acid dissolution enhancer proportions. The formulations may comprise combinations of said organic acid dissolution enhancers, in amounts that individually or in aggregate achieve(s) the stated weight to weight proportions.

In some embodiments, tafamidis-organic acid co-crystal formulations of the present disclosure can include one or more pH adjusting agent(s) and/or buffer(s). pH adjusting agents useful in the compositions of the present disclosure include sodium hydroxide, potassium hydroxide, citric acid, and hydrochloric acid. Buffers useful in formulations of the disclosure include is acetic acid, sodium acetate, benzoic acid, sodium benzoate, boric acid, sodium borate, citric acid, sodium citrate, sodium phosphate, monobasic sodium phosphate, dibasic sodium phosphate, potassium phosphate, monobasic potassium phosphate, dibasic potassium phosphate, sodium acetate, lactic acid, tartaric acid, sodium tartrate, sodium bicarbonate, sodium carbonate, or tris(hydroxymethyl)aminomethane ("TRIS"). Formulations of the present disclosure may contain amounts of pH adjusting agent(s) and/or buffers sufficient to achieve a pH of 4 to 9, for example pH 4, pH 4.1, pH 4.2, pH 4.3, pH 4.4, pH 4.5, pH 4.6, pH 4.7, pH 4.8, pH 4.9, pH 5, pH 5.1, pH 5.2, pH 5.3, pH 5.4, pH 5.5, pH 5.6, pH 5.7, pH 5.8, pH 5.9, pH 6, pH 6.1, pH 6.2, pH 6.3, pH 6.4, pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, pH 8, pH 8.1, pH 8.2, pH 8.3, pH 8.4, pH 8.5. pH 8.6, pH 8.7, pH 8.8, pH 8.9, pH 9, or in a range between any two such pH values.

In some embodiments, formulations of the disclosure can include a polymer. Non-ionic polymers useful in certain formulations of the disclosure include hydroxyethyl cellulose, hydroxypropylmethyl cellulose, methyl cellulose, carboxymethyl cellulose, polyvinyl pyrrolidone, and polyvinyl alcohol. Ionic polymers useful in certain formulations of the disclosure include polyacrylates (e.g., carbopols and carbomers), alginates, chitosans, hyaluronic acid, and xanthan gum. Such ionic and/or nonionic polymers can be present in formulations of the disclosure in weight to weight proportions of the overall formulation of 0.001% w/w, 0.005% w/w, 0.01% w/w, 0.05% w/w, 0.1% w/w, 0.25% w/w, 0.5% w/w, 0.75% w/w, 1.0% w/w, 1.25% w/w, 1.5% w/w, 1.75% w/w, 2.0% w/w, 2.25% w/w, 2.5% w/w, 2.75% w/w, 3.0% w/w, 3.25% w/w, 3.5% w/w 3.75% w/w, 4.0% w/w, 4.25% w/w, 4.5% w/w, 4.75% w/w, and 5.0% w/w, as well as in a range between any two of said polymer proportions. The formulations may comprise combinations of polymers, in amounts that individually or in aggregate achieve(s) the stated polymer proportions.

In some embodiments, formulations of the disclosure can include a surfactant. Surfactants useful in certain formulations of the disclosure include sodium lauryl sulfate, docusate sodium, phosphatidylcholine, lecithin, betaines, tyloxapol, polyoxyethylene sorbitan esters, such as polysorbate 20, polysorbate 60, and polysorbate 80; polyethoxylated castor oils, such as cremaphor, polyethoxylated hydrogenated castor oils, such as HCO-40; and poloxamers. Such surfactants may be present in formulations of the disclosure in weight to weight proportions of the overall formulation of 0.001% w/w, 0.005% w/w, 0.01% w/w, 0.05% w/w, 0.1% w/w, 0.2% w/w, 0.3% w/w, 0.4% w/w, 0.5% w/w, 0.6% w/w, 0.7% w/w, 0.8% w/w, 0.9% w/w, 1.0% w/w, 1.1% w/w, 1.2% w/w, 1.3% w/w, 1.4% w/w, 1.5% w/w, 1.6% w/w, 1.7% w/w, 1.8% w/w, 1.9% w/w, 2.0% w/w, or in a ranges between any two of said surfactant proportions. The formulations may comprise combinations of surfactants, in amounts that individually or in aggregate achieve(s) the stated weight to weight proportions.

In some embodiments, formulations of the present disclosure are pourable. The viscosities of such formulations can range from 1 centipoise ("cps") (i.e., the viscosity of water at room temperature) to 25,000 cps (i.e., the viscosity of chocolate syrup at room temperature); and exemplary particular viscosities of formulations of the disclosure include 1 cps, 25 cps, 50 cps, 75 cps, 100 cps, 150 cps, 200 cps (about the viscosity of maple syrup at room temperature), 250 cps, 300 cps, 400 cps, 500 cps, 600 cps, 700 cps, 800 cps, 900 cps, 1000 cps (about the viscosity of glycerin at room temperature), 1100 cps, 1200 cps, 1300 cps, 1400 cps, 1500 cps, 1600 cps, 1700 cps, 1800 cps, 1900 cps, 2000 cps, 2100 cps, 2200 cps, 2300 cps, 2400 cps, 2500 cps, 2600 cps, 2700 cps, 2800 cps, 2900 cps, 3000, 3500 cps, 4000 cps, 4500 cps, 5000 cps, 6000 cps, 7000 cps, 8000 cps, 9000 cps, 10,000 cps, 12,500 cps, 15,000 cps, 17,500 cps, 20,000 cps 22,500 cps, 25,000 cps (about the viscosity of chocolate syrup at room temperature), 27,500 cps, 30,000, cps as well as in a range between any two of said viscosities.

In some embodiments, formulations of the disclosure can include a sweetener. Sweeteners useful in the formulations of the present disclosure include acesulfame-K, advantame, alitame, aspartame, brazzein, carrelame, curculin, cyclamic acid, corn syrup (e.g., high fructose corn syrup), cyclamate, dihydrochalchone, erythritol, fructose, galactose, glucose, glycerin, glycine, glycyrrhizic acid, hydrogenated glucose syrup, hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, stevia glycosides, sucralose, sucrose, tagatose, tryptophan, and xylitol. The sweetener may be present in liquid pharmaceutical formulations of the disclosure in weight to volume proportions of 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said sweetener proportions. The formulations may comprise combinations of sweeteners, in amounts that individually or in aggregate achieve(s) the stated weight to volume proportions.

In some embodiments, formulations of the disclosure can include a flavorant. Flavorants useful in the formulations of the present disclosure include chocolate, vanilla, caramel, orange, lemon, lime, strawberry, raspberry, blueberry, cherry, cinnamon, and nutmeg. The flavorant may be present in liquid pharmaceutical formulations of the disclosure in weight to volume proportions of 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said flavorant proportions. The formulations may comprise combinations of flavorant, in amounts that individually or in aggregate achieve(s) the stated weight to volume proportions In some embodiments, formulations of the disclosure can include a tonicity agent. Ionic tonicity agents useful in certain formulations of the disclosure include calcium chloride, magnesium chloride, potassium chloride, sodium chloride, sodium sulfate, and combinations thereof. Nonionic tonicity agents useful in the formulations described herein include mannitol, sorbitol, xylitol, erythritol, lactitol, maltitol, isomalt, and combinations thereof. The formulations may comprise tonicity agent in weight to weight proportions of the overall formulation of 0.001% w/w, 0.005% w/w, 0.01% w/w, 0.05% w/w, 0.1% w/w, 0.2% w/w, 0.3% w/w, 0.4% w/w, 0.5% w/w, 0.6% w/w, 0.7% w/w, 0.8% w/w, 0.9% w/w, 1.0% w/w, 1.1% w/w, 1.2% w/w, 1.3% w/w, 1.4% w/w, 1.5% w/w, 1.6% w/w, 1.7% w/w, 1.8% w/w, 1.9% w/w, 2.0% w/w, or in a range between any two of said tonicity agent proportions. The formulations may comprise combinations of tonicity agent, in amounts that individually or in aggregate achieve(s) the stated tonicity agent proportions.

In some embodiments, formulations of the disclosure can include a preservative. Preservatives useful in certain formulations of the disclosure include dibutylhydroxytoluene, benzalkonium chloride, benzyl alcohol, borates, parabens, cresols, benzoic acid, phenol, sorbic acid, benzethonium chloride, sodium chlorite and combinations thereof. The formulations may comprise preservative in weight to weight proportions of the overall formulation of 0.001% w/w, 0.005% w/w, 0.01% ow/w, 0.05% w/w, 0.1% w/w, 0.25% w/w, 0.5% w/w, 0.75% w/w, 1.0% w/w, 1.25% w/w, 1.5% w/w, 1.75% w/w, 2.0% w/w, 2.25% w/w, 2.5% w/w, 2.75% w/w, 3.0% w/w, 3.25% w/w, 3.5% w/w 3.75% w/w, 4.0% w/w, 4.25% w/w, 4.5% w/w, 4.75% w/w, and 5.0% w/w, or in a range between any two of said preservative proportions. The formulations may comprise combinations of preservatives, in amounts that individually or in aggregate achieve(s) the stated weight to weight proportions.

A preferred preservative is dibutylhydroxytoluene, preferably added in an amount of from 0.05% w/w to 1.0% w/w.

EXAMPLES

Aspects of embodiments of the present disclosure may be further understood in light of the following examples, which should not be construed as limiting in any way.

Example 1

Dissolution studies overview. The objective of the dissolution studies of the present disclosure was to evaluate the rate and extent of tafamidis dissolution from formulations in relevant media (e.g., FaSSIF and FeSSIF). Prototype tafamidis formulations A, B.1, B.2, C.1, and C.2 comprised the ingredients specified in Table 1.1 and were studied in the dissolution experimental protocol described in this Example 1. The dissolution experimental results stated in Tables 1.5 and 1.6. indicated that pharmaceutical formulations of the current disclosure possess increased rate and/or extent of dissolution.

TABLE 1.1

Tafamidis formulations

| Ingredient | Prototype A mg/cap | Prototype A % w/w | Prototype B mg/cap | Prototype B % w/w | Prototype B.1 mg/cap | Prototype B.1 % w/w | Prototype C mg/cap | Prototype C % w/w | Prototype C.1 mg/cap | Prototype C.1 % w/w |
|---|---|---|---|---|---|---|---|---|---|---|
| Tafamidis-fumaric acid co-crystal | 72.5 | 10.19 | 72.5 | 10.19 | 72.5 | 10.19 | 72.5 | 10.19 | 72.5 | 10.19 |
| PEG 400 | 568.4 | 79.89 | 477.4 | 67.10 | 633.7 | 89 | 572.4 | 80.4 | 581.9 | 81.79 |
| Fumaric acid | 0 | 0 | 19 | 2.67 | 4.75 | 0.67 | 19 | 2.67 | 9.5 | 1.34 |
| Povidone K 90 | 12 | 1.7 | 24 | 3.37 | 0 | 0 | 8 | 1.1 | 8 | 1.1 |
| BHT | 0.6 | 0.08 | 0.6 | 0.08 | 0.6 | 0.08 | 0.6 | 0.08 | 0.6 | 0.08 |
| Polysorbate 20 | 58 | 8.2 | 118 | 16.58 | 0 | 0 | 39 | 5.5 | 39 | 5.5 |
| Total | 711.5 | 100.00 | 711.5 | 100.00 | 711.5 | 100.00 | 711.5 | 100.00 | 711.5 | 100.00 |

Manufacture of formulations. The process steps by which the tafamidis prototype formulations were manufactured was as follows. The required quantity of PEG 400 was placed in a vessel having a magnetic stir bar. Then, the required quantities of polysorbate 20 and BHT were added to the PEG 400 under continuous stirring and further stirred until a clear solution was obtained. To the resultant solution, the required quantity of Povidone K 90 was added under continuous stirring and further stirred until a clear solution was obtained. To the resultant solution, the required quantities of fumaric acid and tafamidis cocrystal were added under continuous stirring and further stirred or subjected to high sheer homogenization until uniform distribution of the tafamidis was obtained, which yielded the formulation ready for encapsulation.

Dissolution experimental protocol. The general conditions of the dissolution experiments of the present disclosure were as set forth in Table 1.2.

TABLE 1.2

Dissolution experiments general conditions

| | |
|---|---|
| Media: | FaSSIF-V2 Biorelavant.com Product Code: V2FAS-0821-A |
| | FeSSIF-V2 Biorelavant.com Product Code: V2FES-0322-A |
| Volume: | 900 mL |
| Speed: | 75 RPM |
| Apparatus: | USP apparatus II (Paddle) with sinker (Electrolab, Model EDT-08LX, Sampler: ESC-08D) |
| Time points : | 0, 15, 20, 30, 45, 60, 90, 120 minutes + recovery |
| Temperature : | 37° C. + 0.5° C. |

Dissolution media: Modified FeSSIF pH 5.8. 5.5 g of sodium chloride, 2.4 g of sodium hydroxide, and 4.8 g of maleic acid were transferred into 900 ml of milli Q water and sonicated to dissolve. The resulting solution was adjusted to pH 5.8 with 1.0 M sodium hydroxide. 7.3 g of FeSSIF-V2 was added into the same solution and sonicated to dissolve. The pH of the media was checked and adjusted to pH 5.8 with 1.0 M sodium hydroxide if necessary. The solution was diluted up to 1000 ml mark with milli Q water. The pH of the solution was checked and adjusted to pH 5.8 with 1.0 M sodium hydroxide if necessary.

Dissolution media: Modified FaSSIF pH 6.5. 4 gm of sodium chloride, 1.35 g of sodium hydroxide, and 2.3 g of maleic acid were transferred into 900 ml of milli Q water and sonicated to dissolve. The resulting solution was adjusted to pH 6.5 with 1.0 M sodium hydroxide. 1.84 g of FaSSIF-V2 buffer was added into the same solution and sonicated to dissolve. 1 g of polysorbate-80 was added and mixed well. The pH of the solution was checked and adjusted to pH 6.5 with 1.0 M sodium hydroxide if necessary. The solution was diluted up to 1000 ml with milli Q water. The pH of the solution was checked and adjusted to pH 6.5 with 1.0 M sodium hydroxide if necessary.

Dissolution experiment. Dissolution medium (900 mL) was placed in the vessel of the dissolution apparatus and equilibrated to 37° C.±0.5° C. One capsule for each of tafamidis prototype formulation A, B.1, B.2, C.1, C.2 was placed in the sinker of the dissolution apparatus, immersed into the vessel, and the apparatus was then operated at 75 RPM. At each of the specified time points, 10 ml of the dissolution medium was withdrawn from the vessel. The withdrawn dissolution media was filtered through 0.45 µm PVDF filter, the first 2.0 ml of filtrate was discarded.

Dissolution HPLC chromatogaphy reagents. The high-pressure liquid chromatography ("HPLC") buffers and columns employed in the dissolution experiments of the present disclosure were as set forth in Table 1.3.

TABLE 1.3

HPLC chromatography reagents and columns

| | |
|---|---|
| Dilute orthophosphoric acid solution: | 10 ml orthophosphoric acid into 100 ml water |
| Buffer: | Add 1.56 g of sodium dihydrogen phosphate monohydrate into 1000 ml of water. Adjust to pH 3.3 + 0.05 with dilute orthophosphoric acid solution. Filter through 0.45 um membrane filter and degas. |
| Organic mixture: | Mix 50:50 (v/v) acetonitrile : methanol and degas |
| Blank: | Mix 1:20 (v/v) dissolution medium : diluent. |
| Standard solution I: | Add 20 mg of tafamidis-fumaric acid co-crystal standard to 3 ml tetrahydrofuran, sonicate until dissolved, and bring to 100 ml with dissolution media. Pipette 2.0 ml of the resulting solution into a 100 ml volumetric flask bring to 100 ml with diluent. |
| Sample solution: | Mix 1:20 (v/v) retained filtrate* : diluent. |
| Standard solution II | Independently made replicate of standard solution I. |
| Mobile phase buffer: | Mix 30:70 (v/v) buffer : organic mixture and degas |
| Diluent : | Mix 80:20 (v/v) methanol : water and degas. |
| HPLC column: | Waters XBridge C18 50 mm × 4.6 mm, 3.5 um |
| Column temperature : | 40° C. |
| Sample temperature : | 15° C. |
| Flow rate: | 1 ml/min |
| Ultraviolet detector: | Waters, Separation Module e2695, UV Detector: 2489 UV/Visible, 310 nm |
| Injection volume: | 10 ul |
| Run time: | 10 min |

*Note that the retained filtrate is described in the dissolution experiment section of Example 1.

HPLC chromatography procedure (tafamidis assay). IPLC runs were performed in isocratic mode and in accordance with parameters set forth in above Table 1.3 on blank solution (one replicate), standard solution I (five replicates), and standard solution II (two replicates). The peak responses due to tafamidis were recorded and the similarity factor between standard preparations were calculated by the formula set forth in Table 1.4. IPLC tafamidis assay runs were also performed according to parameters set forth in above Table 1.3 on samples (six replicates) and the percent tafamidis dissolved in each sample was calculated by the formula set forth in Table 1.4. The results of the IPLC tafamidis assay of the dissolution experiments of this Example 1 are set forth in Table 1.5 and Table 1.6.

TABLE 1.4

Tafamidis assay equations $$\text{Standard solution similarity factor} = \frac{\text{Average area of standard solution I} \times \text{Concentration of standard solution II}}{\text{Average area of standard solution II} \times \text{Concentration of standard solution I}}$$

$$\text{Percent dissolved tafamidis} = \frac{Asok}{Aspd} \times \frac{Wtsd}{100\ ml} \times \frac{2.0\ ml}{100\ ml} \times \frac{900\ ml}{1\ Cap} \times \frac{20\ ml}{1.0\ ml} \times \frac{P\ (\%)}{LC\ (mg)} \times \frac{308.12}{366.16}$$

Aspl: Area of tafamidis obtained in the sample solution.
Astd: Average area responses of five replicate injections of tafamidis obtained ir standard solution I.
Wstd: Weight of the Tafamidis Co-Crystal working standard in mg.
P: Purity of tafamidis-fumaric acid co-crystal working standard on as is basis ir percentage.
LC: Label claim of tafamidis in mg/capsule.
366.16: Molecular weight of tafamidis-fumaric acid co-crystal.
308.12: Molecular weight of tafamidis.

TABLE 1.5

Tafamidis dissolution assay conducted in Modified FeSSIF pH 5.8 @ 900 RPM, 37° C.

| Tafamidis formulation | 15 min | 20 min | 30 min | 45 min | 60 min | 90 min | 120 min | Recovery |
|---|---|---|---|---|---|---|---|---|
| Prototype A | 61 | 60 | 64 | 65 | 65 | 65 | 65 | 65 |
| Prototype B | 82 | 83 | 86 | 88 | 89 | 91 | 91 | 91 |
| Prototype B.1 | 59 | 60 | 61 | 61 | 61 | 62 | 64 | 63 |
| Prototype C | 91 | 95 | 96 | 94 | 97 | 96 | 96 | 97 |
| Prototype C.1 | 90 | 93 | 94 | 95 | 95 | 95 | 96 | 97 |

TABLE 1.6

Tafamidis dissolution assay conducted in Modified FaSSIF pH 6.5 @ 900 RPM, 37° C.

| Tafamidis formulation | 15 min | 20 min | 30 min | 45 min | 60 min | 90 min | 120 min | Recovery |
|---|---|---|---|---|---|---|---|---|
| Prototype A | 75 | 76 | 79 | 79 | 79 | 79 | 80 | 81 |
| Prototype B | 83 | 87 | 89 | 90 | 92 | 90 | 91 | 91 |
| Prototype B.1 | 59 | 63 | 66 | 68 | 71 | 74 | 75 | 72 |
| Prototype C | 86 | 90 | 91 | 90 | 91 | 91 | 91 | 92 |
| Prototype C.1 | 92 | 94 | 94 | 95 | 95 | 95 | 95 | 94 |

While the foregoing specification teaches the principles of the present invention, with examples provided for the purpose of illustration, it will be understood that the practice of the invention encompasses all variations, adaptations and/or modifications as come within the scope of the following claims and their equivalents.

What is claimed is:

1. A pharmaceutical, unit-dose formulation, suitable for oral administration, comprising:
   from 1% w/w to 20% w/w of a tafamidis-fumaric acid co-crystal;
   from 0.25% w/w to 2.5% w/w of an added organic acid dissolution enhancer;
   from 77.5% w/w to 82.5% w/w of a polyethylene glycol (PEG), wherein the PEG has a molecular weight of 100 to 1000;
   from 1% w/w to 10% w/w of a polysorbate that is polysorbate 20, polysorbate 40, polysorbate 60, polysorbate 80, or a combination thereof; and
   from 0.25% w/w to 2.75% w/w of a polyvinylpyrrolidone (PVP), wherein the PVP has a K value of 10 to 120;
   wherein the formulation releases, within 15 minutes in modified FeSSIF pH 5.8 or in modified FaSSIF pH 6.5, at least 85% of the total tafamidis of the formulation, and
   wherein the formulation releases, within 45 minutes in modified FeSSIF pH6.5, at least 90% of the total tafamidis of the formulation.

2. The formulation of claim 1, wherein the organic acid dissolution enhancer is acetic acid, adipic acid, ascorbic acid, benzoic acid, butanoic acid, citric acid, formic acid, fumaric acid, maleic acid, glutaric acid, hexanedioic acid, lactic acid, malonic acid, trichloroacetic acid, oxalic acid, propionic acid, sorbic acid, tartaric acid, and succinic acid, or a combination of at least two of any thereof.

3. The formulation of claim 2, wherein the PEG is the PEG 400, the PVP is PVP K90, and the polysorbate is the polysorbate 20.

4. The formulation of claim 3, wherein the formulation releases, within 15 minutes in modified FeSSIF pH 5.8 or in modified FaSSIF pH 6.5, at least 90% of the total tafamidis of the formulation.

5. A method of treating cardiomyopathy or peripheral neuropathy arising from transthyretin amyloidosis, comprising orally administering the unit-dose formulation of claim 1 to a subject presenting cardiomyopathy or peripheral neuropathy arising from transthyretin amyloidosis.

6. The method of claim 5, wherein the formulation is administered to the subject once daily and wherein the unit-dose formulation comprises from 10 mg to 80 mg of the tafamidis-fumaric acid co-crystal.

7. A pharmaceutical, unit-dose formulation, suitable for oral administration, comprising:
   from 1% w/w to 20% w/w of a tafamidis-fumaric acid co-crystal;

from 77.5% w/w to 82.5% w/w of a PEG that has a molecular weight of 100 to 1000;

from 0.25% w/w to 2.5% w/w of an added organic acid dissolution enhancer that is fumaric acid;

from 0.25% w/w to 2.75% w/w of a PVP, wherein the PVP has a K value of 10 to 120;

from 1% w/w to 10% w/w of a polysorbate that is polysorbate 20, polysorbate 40, polysorbate 60, polysorbate 80, or a combination thereof; and from 0.05% w/w to 0.25% w/w of a dibutylhydroxytoluene, wherein the formulation releases, within 15 minutes in modified FeSSIF pH 5.8 or in modified FaSSIF pH 6.5, at least 85% of the total tafamidis of the formulation, and wherein the formulation releases, within 45 minutes in modified FeSSIF pH6.5, at least 90% of the total tafamidis of the formulation.

8. The formulation of claim 7, further comprising from 0.05% w/w to 0.25% w/w of a dibutylhydroxytoluene, wherein:

the PEG has the molecular weight of 400, the PVP has a K value of 90, the polysorbate is the polysorbate 20.

9. A pharmaceutical, unit-dose formulation, suitable for oral administration, comprising:

from 7.5% w/w to 12.5% w/w of a tafamidis-fumaric acid co-crystal;

from 77.5% w/w to 82.5% w/w of a PEG 400;

from 0.25% w/w to 2.5% w/w of a fumaric acid;

from 0.25% w/w to 2.75% w/w of a PVP K 90;

from 1% w/w to 10% w/w of a polysorbate 20; and from 0.05% w/w to 0.25% w/w of a dibutylhydroxytoluene, wherein the formulation releases, within 15 minutes in ¾ strength FeSSIF pH 5.8 or in FaSSIF+0.1% polysorbate 80 pH 6.5, at least 85% of the total tafamidis of the formulation, and wherein the formulation releases, within 45 minutes in modified FeSSIF pH6.5, at least 90% of the total tafamidis of the formulation.

10. The formulation of claim 1, wherein the PVP is present at 1.1% w/w, and wherein the polysorbate is present in at 3.3% w/w.

11. The formulation of claim 7, wherein the PVP is present at 1.1% w/w, and wherein the polysorbate is present in at 3.3% w/w.

12. The formulation of claim 7, wherein the PVP is present at 1.1% w/w, and wherein the polysorbate is present in at 3.3% w/w.

* * * * *